United States Patent [19]

Hovestadt et al.

[11] Patent Number: 5,688,891

[45] Date of Patent: Nov. 18, 1997

[54] 1,3-DIOXAN-2-ONE GROUP-CONTAINING OLIGOURETHANES

[75] Inventors: Wieland Hovestadt; Hans-Josef Buysch, both of Krefeld; Lutz Schmalstieg, Köln; Harald Blum, Wachtendonk; Norbert Schön, Darmstadt, all of Germany

[73] Assignee: Bayer Aktiengesellschaft, Leverkusen, Germany

[21] Appl. No.: 523,977

[22] Filed: Sep. 6, 1995

[30] Foreign Application Priority Data

Sep. 14, 1994 [DE] Germany ............ 44 32 647.5

[51] Int. Cl.⁶ .................. C08G 64/02; C07D 319/06
[52] U.S. Cl. .................. 528/73; 528/49; 549/228
[58] Field of Search ............ 549/228; 528/73, 528/49

[56] References Cited

U.S. PATENT DOCUMENTS

| | | | |
|---|---|---|---|
| 4,440,937 | 4/1984 | Krimm et al. | 549/228 |
| 4,501,905 | 2/1985 | Krimm et al. | 549/228 |

FOREIGN PATENT DOCUMENTS 3418092  11/1985  Germany.

OTHER PUBLICATIONS

Makromolekulare Chemie, Macromolecular Symposia, vol. 42/43, Mar. 1991, Basel Ch, pp. 145–153, H. Höcker et al, 'Ring–Opening Polymerization and Copolymerization of Cyclic Carbonates'.

*Primary Examiner*—Jose G. Dees
*Assistant Examiner*—Laura L. Stockton
*Attorney, Agent, or Firm*—Joseph C. Gil; Thomas W. Roy

[57] ABSTRACT

Described herein is a process for the preparation of 1,3-dioxan-2-one group-containing oligourethanes by reacting a) hydroxy-functional 1,3-dioxan-2-ones with b) compounds having an average of at least two isocyanate groups per molecule; the oligourethanes obtainable by this process; and their use, optionally in combination with compounds containing active hydrogen atoms, for the preparation of plastics or as a binder or binder component in coating compositions.

13 Claims, No Drawings

1,3-DIOXAN-2-ONE GROUP-CONTAINING OLIGOURETHANES

BACKGROUND OF THE INVENTION

1. Field of the Invention

The present invention relates to a process for the preparation of 1,3-dioxan-2-one group-containing oligourethanes by reacting hydroxy-functional 1,3-dioxan-2-ones with organic polyisocyanates; to the oligourethanes obtained by this process; and to their use in coating compositions or for the preparation of plastics.

2. Description of the Prior Art

Polyurethane resins or mixtures of organic polyisocyanates and organic polyhydroxyl compounds which react to form polyurethane resins, enjoy widespread use in almost every industrial sector, in particular for the production of coatings, due to the properties that they possess, which may be varied over a broad range. Some of the disadvantages of these polyurethanes are their sensitivity to moisture, which frequently necessitates taking particular precautions in the preparation of non-porous plastics or coatings, and the need, when manufacturing stoving lacquers which remain stable when stored at room temperature, to utilize blocked polyisocyanates which release blocking agents.

An object of the present invention is to provide novel plastics precursors that provide products having the wide range of properties known from polyurethane chemistry due to the ability to use a wide variety of starting materials without the aforementioned disadvantages.

This object may be achieved with the 1,3-dioxan-2-one group-exhibiting oligourethanes according to the invention, which are described hereinafter. The products according to the invention represent plastics precursors that may be polymerized to form high molecular weight plastics without release of blocking agents and may also be reacted with a very wide variety of isocyanate-reactive compounds to form high molecular weight cross-linked polyaddition products. The variation of the properties of the polyaddition products being attributable not only to the variability of the isocyanate-reactive compounds, but also to the wide variety of starting materials that may be utilized to produce the oligourethanes themselves.

SUMMARY OF THE INVENTION

The present invention relates to a process for the preparation of 1,3-dioxan-2-one group-containing oligourethanes by reacting a) hydroxy-functional 1,3-dioxan-2-ones corresponding to the formula

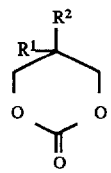

wherein
  $R^1$ represents a hydroxyalkyl radical and
  $R^2$ represents an alkyl radical with b) compounds containing an average of at least two isocyanate groups per molecule to form urethane groups.

The present invention also related to the oligourethanes obtained by this process and to their use, optionally in combination with isocyanate-reactive compounds, for the preparation of high molecular weight plastics or as a binder or binder component in coating compositions.

DETAILED DESCRIPTION OF THE INVENTION

The hydroxy-functional 1,3-dioxan-2-ones that may be utilized as component a) according to the invention are known and described, for example, in EP-A 0,057,360 (U.S. Pat. No. 4,501,905, herein incorporated by reference) or DE-OS 3,418,092. Examples of these compounds include those corresponding to formula (I)

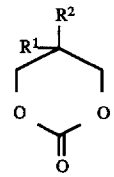

wherein
  $R^1$ represents a hydroxyalkyl radical preferably having 1 to 10, more preferably 1 to 4 carbon atoms, and
  $R^2$ represents an alkyl radical preferably having 1 to 4, more preferably 1 or 2 carbon atoms.

1,3-dioxan-5-hydroxymethyl-5-methyl-2-one or 1,3-dioxan-5-hydroxymethyl-5-ethyl-2-one are especially preferred for use as component a).

Component b) is selected from organic compounds containing at least 2 isocyanate groups per molecule. Examples of these organic polyisocyanates include (i) monomeric organic polyisocyanates having a molecular weight of 140 to 300, (ii) lacquer polyisocyanates having a molecular weight of greater than 300 to 1,000, (iii) urethane group-containing NCO prepolymers having a molecular weight of greater than 1,000 and (iv) mixtures of the preceding polyisocyanates.

Examples of group (i) polyisocyanates include 1,4-diisocyanatobutane, 1,6-diisocyanatohexane (HDI), 1,5-diisocyanato-2,2-dimethylpentane, 2,2,4- or 2,4,4-trimethyl-1,6-diisocyanatohexane, 1-isocyanato-3,3,5-trimethyl-5-isocyanatomethyl cyclohexane (IPDI), 1-isocyanato-1-methyl-4-(3)-isocyanatomethyl cyclohexane, 1,3-diisocyanato-6-methylcyclohexane, bis(4-isocyanatocyclohexyl) methane, 1,10-diisocyanatodecane, 1,12-diisocyanatododecane, cyclohexane-1,3- and -1,4-diisocyanate, the xylylene diisocyanate isomers, 2,4-diisocyanatotoluene and mixtures thereof with preferably up to 35 wt-%, based on the weight of the mixture, of 2,6-diisocyanatotoluene, and 2,2'-, 2,4'- or 4,4'-diisocyanatodiphenylmethane or polyisocyanate mixtures of the diphenylmethane series, mixtures of the preceding isocyanates. Preferred group (i) polyisocyanates are HDI and IPDI.

Group (ii) polyisocyanates are the known lacquer polyisocyanates. In accordance with the present invention the term "lacquer polyisocyanates" means compounds or mixtures of compounds prepared by the known oligomerization reactions of monomeric diisocyanates, such as those previously set forth as group (i) polyisocyanates. Examples of these oligomerization reactions include carbodiimidization, dimerization, trimerization, biuretization, urea formation, urethanization, allophanatization and/or cyclization with formation of oxadiazine structures. It is frequently the case during "oligomerization" that a number of the these reactions take place simultaneously or sequentially.

Preferred "lacquer polyisocyanates" are a) biuret polyisocyanates, b) polyisocyanates containing isocyanurate groups, c) polyisocyanate mixtures containing isocyanurate groups and uretdione groups, d) polyisocyanates containing urethane groups and/or allophanate groups and e) polyisocyanate mixtures containing isocyanurate groups and allophanate groups. These lacquer polyisocyanates may be prepared from the previously listed monomeric diisocyanates, preferably HDI or IPDI and more preferably HDI.

The preparation of these lacquer polyisocyanates is known and described, for example, in DE-OS 1,595,273, DE-OS 3,700,209, DE-OS 3,900,053, EP-A-0,330,966, EP-A-0,259,233, EP-A-0,377,177, EP-A-0,496,208, EP-A-0,524,501 and U.S. Pat. No. 4,385,171.

Group (iii) polyisocyanates are the known prepolymers containing isocyanate groups and prepared from monomeric diisocyanates, e.g., those suitable for use as group (i) polyisocyanates, and/or lacquer polyisocyanates previously set forth and organic polyhydroxyl compounds having a molecular weight greater than 300. The group (iii) prepolymers may be distinguished from the group (ii) lacquer polyisocyanates containing urethane groups based on the molecular weight of the polyol. The group (ii) lacquer polyisocyanates are exclusively prepared from low molecular weight polyols having a molecular weight of 62 to 300, such as ethylene glycol, propylene glycol, trimethylolpropane, glycerol and mixtures thereof.

To the contrary the group (iii) NCO prepolymers are prepared from polyhydroxyl compounds having a molecular weight greater than 300, preferably greater than 500, more preferably 500 to 4,000. These polyhydroxyl compounds preferably have 2 to 6, more preferably 2 to 3, hydroxyl groups per molecule and are selected from polyether polyols, polyester polyols, polythioether polyols, polycarbonate polyols, polyacrylate polyols and mixtures thereof.

These higher molecular weight polyols may also be used in admixture with low molecular weight polyols previously set forth when preparing NCO prepolymers (iii), such that mixtures of low molecular weight lacquer polyisocyanates (ii) containing urethane groups and higher molecular weight NCO prepolymers (iii) are directly prepared.

In order to prepare the NCO prepolymers (iii) or the mixtures thereof with the lacquer polyisocyanates (ii), the group (i) diisocyanates or the group (ii) lacquer polyisocyanates are reacted with the higher molecular weight polyhydroxyl compounds or mixtures thereof with low molecular weight polyhydroxyl compounds at an NCO/OH equivalent ratio of 1.1:1 to 40:1, preferably 2:1 to 25:1 to form urethane groups.

When an excess of distillable diisocyanate starting compound (i) is used, the latter excess may be optionally be removed by distillation at the end of the reaction such that monomer-free NCO prepolymers are produced. If group (i) diisocyanates are utilized in excess as the isocyanate component and are not removed, NCO semi-prepolymers [i.e., mixtures of group (i) diisocyanates and group (iii) NCO prepolymers] are present which may be utilized as the starting component b) according to the invention.

Suitable selection of the type of component b) to be utilized in the process according to the invention, enables the attributes of the resulting products to be matched to the desired application. It is also possible to vary the high molecular weight plastics or coatings which are finally obtained from the products according to the invention by the suitable selection of the isocyanate-reactive compounds utilized as co-reactants for the oligourethanes according to the invention.

In the process according to the invention, the starting components a) and b) are utilized in quantities which correspond to an OH/NCO equivalent ratio of 0.5:1 to 2:1, preferably 0.9:1 to 1.1:1 and more preferably 1:1.

The reaction may be carried out either solvent-free or in a suitable aprotic solvent or solvent mixture. Examples include toluene, xylene, butyl acetate, ethyl acetate, ethyl glycol acetate, pentyl acetate, hexyl acetate, methoxypropyl acetate, tetrahydrofuran, dioxan, dibutyl diglycol, acetone, methyl ethyl ketone, methyl isobutyl ketone, cyclopentanone, cyclohexanone, N-methyl-pyrrolidone, dimethyl formamide, higher-substituted aromatics (such as solvent naphtha, heavy benzole, the Solvesso solvents and Diasol solvent) and higher-boiling aliphatic and cycloaliphatic hydrocarbons (such as white spirits, mineral oil of turpentine, Ispar solvents, Nappar solvents, tetralin and decalin).

The reaction is generally conducted at a temperature of 20° to 130° C., preferably 40° to 100° C. The solvent is present in an amount sufficient to provide a concentration of starting components a) and b) of 0 to 80, preferably 0 to 50 wt-%.

In order to accelerate the reaction between component a) and component b), catalysts may optionally be used. Examples include triethylamine, tributylamine, 1,4-diazabicyclo-(2,2,2)-octane, N,N-dimethyl benzylamine, 2-methyl imidazole, pyridine, Mannich bases, tetraalkylammonium hydroxides, alkali metal hydroxides (such as lithium hydroxide and sodium hydroxide), alkali metal phenolates, metal salts (such as iron(III) chloride) and tin compounds (such as tin(II) acetate, tin(II) octoate, tin(II) ethyl hexanoate, tin(II) laurate, dibutyltin oxide, dibutyltin dichloride, dibutyltin diacetate, dibutyltin dilaurate, dibutyltin maleate and diocyltin diacetate).

The 1,3-dioxan-2-one group-containing oligourethanes according to the invention are suitable for preparing plastics or coatings. They are processed either as one-component stoving systems or in combination with suitable curing agents as two-component systems.

When they are used as one-component stoving systems, catalysts may be added which are known to catalyze the ring-opening polymerization of 1,3-dioxan-2-ones (cf., for example, EP-A-0,209,722, EP-A-0,188,204, DE-OS 1,545,116, DE-OS 1,545,117, DE-OS 1,545,118 or JACS 52 (1930) 314. These include the catalysts previously set forth and also reaction products of alkyl phosphates or alkyl phosphonates with phosphines, amines, amides or N-heterocyclic compounds; alkali metal alcoholates; alkali metal carboxylates; acid amides; ureas; and amidines.

When the oligourethanes according to the invention are used as binders in stoving lacquers, they are cured at a temperature of 80° to 180° C.

When the oligourethanes according to the invention are used in two-component systems, any compounds having at least two Zerewitinoff-active hydrogen atoms groups may be used as co-reactants. Examples of suitable compounds include polycarboxylic acids, hydroxycarboxylic acids, polyanhydrides, polyhydroxyl compounds, polyamines, aminoalcohols, aminoacids and polyurethanes having at least two active hydrogen atoms. The isocyanate-reactive compounds may be either low molecular weight and higher molecular weight. It is also possible to use compounds having potential H-active groups, for example moisture-activatable groups, such as bis-ketimines, bis-aldimines or polyoxazolidines. The co-reactants may be used in an amount which are, in relation to the dioxanone groups, approximately equivalent or markedly deficient. Depending on reactivity, curing takes place by addition of the curing agent with opening of the 1,3-dioxan-2-one group rings at temperatures of between 0° and 180° C.

When the oligourethanes according to the invention are used according to the invention as binders or binder components in coating compositions, known additives may also be used. Examples include flow aids (for example those based on cellulose ester or oligoacrylate), pigments and fillers, viscosity-regulating additives such as bentonites and silicic acid esters, matting agents such as silicic acid, aluminum silicates and high molecular weight waxes, and catalysts for the cross-linking reaction (such as tin(II) octoate, dibutyltin oxide, triethylamine or sodium hydroxide).

In the following examples all parts and percentages are by weight, unless otherwise indicated.

EXAMPLES

Example 1

Preparation of 1,3-dioxan-5-hydroxymethyl-5-ethyl-2-one 1,608 kg (12 moles) of trimethylolpropane, 1,416 kg (12 moles) of diethyl carbonate and 300 mg of powdered KOH were heated to an internal temperature of 110° to 130° C., with stirring, in a 1.2 m packed column for 4 hours. 1,065 kg of ethanol distilled off at the top, with removal of the ethanol by step-wise pressure reduction to 25 mbar towards the end of the esterification. 924 mg of p-toluene sulphonic acid were added to the crude product at an internal temperature of 100° C., and the batch was stirred at this temperature for 30 minutes. The polycarbonate thus obtained was dispensed dropwise from a dropping funnel heated to 150° C. into a flask preheated to 220° C. containing 1.5 g of tin grindings, depolymerized with stirring at a pressure of 0.05 mbar, and the resulting vapors were condensed in cold traps arranged in series (cooled with methanol/dry ice or liquid nitrogen). 1,730 kg (90% of theoretical yield) of a colorless condensate that crystallized at room temperature were obtained.

Example 2

222 g (1 mole) of 1-isocyanato-3,3,5-trimethyl-5-isocyanatomethyl cyclohexane (IPDI) and 0.1 g of dibutyltin oxide dissolved in 200 g of butyl acetate were placed in a three-neck flask equipped with a stirrer, dropping funnel and thermometer, and were heated to 70° C. Within 1 hour, 324 g (2 moles) of 1,3-dioxan-5-hydroxymethyl-5-ethyl-2-one from Example 1, dissolved in 200 g of butyl acetate, were added to this solution. The reaction was complete after 5 hours. A solution of an oligourethane according to the invention having two dioxanone groups per molecule was obtained.

Example 3

100 g of N-methylpyrrolidone, 100 g (0.62 moles) of 1,3-dioxan-5-hydroxymethyl-5-ethyl-2-one from Example 1 and 122 g of an HDI-based lacquer polyisocyanate containing isocyanurate groups and having an NCO content of 21.8% (Desmodur N 3300 available from Bayer AG) were reacted in a three-neck flask with a stirrer, dropping funnel and thermometer. The reaction was complete after 8 hours at 70° C. An oligourethane according to the invention having more than 3 dioxanone groups per molecule was obtained.

Example 4

81 g (0.50 moles) of 1,3-dioxan-5-hydroxymethyl-5-ethyl-2-one from Example 1 and 200 g (0.50 moles NCO) of an NCO prepolymer were weighed into a three-neck flask equipped with a stirrer, dropping funnel and thermometer, and were heated to 70° C. The reaction was complete after 7 hours. An oligourethane according to the invention having more than two 1,3-dioxanone groups per molecule was obtained. The NCO prepolymer was based on an aliphatic lacquer polyisocyanate, i.e., Desmodur N 3300, and a polyester polyol prepolymer, was present as a 65% solution dissolved in solvent naphtha/methoxypropyl acetate (3.8:1), had an NCO content of 10.4%, based on solution, and is available from Bayer AG as Desmodur 3265.

Example 5

100 g of a hydroxy-functional polyacrylate present as a 50% solution in butyl acetate and having an OH content of 1.1%, based on solution (Desmophen A 450 available from Bayer AG), were added to 100 g of the product from Example 2. The mixture was stable in storage. It was applied to a metal test sheet. A hard, solvent-resistant coating was obtained within 30 minutes at 155° C.

Example 6

17 g of N,N'-dimethyl ethylenediamine were added to 100 g of the product from Example 3, followed by application to a metal test sheet. A hard, solvent-resistant coating obtained within 30 minutes at 80° C.

Example 7

20 g of hexamethylene diamine in 50 g of methoxypropyl acetate were added to 100 g of the product from Example 4, followed by application to a metal test sheet. A hard, solvent-resistant coating was obtained within 30 minutes at 80° C.

Example 8

1 g of a 3% solution of potassium-tert.-butylate in s-caprolactam was added to 100 g of the product from Example 3, followed by application to a metal test sheet. A solvent-resistant cured coating was obtained within 30 minutes at 160° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a 1,3-dioxan-2-one group-containing oligourethane which comprises reacting a) one or more hydroxy-functional 1,3-dioxan-2-ones corresponding to the formula

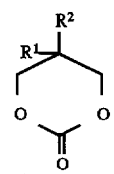

wherein
   $R^1$ represents a hydroxyalkyl radical and
   $R^2$ represents an alkyl radical with b) a polyisocyanate component having an average of at least two isocyanate groups per molecule and containing one or more polyisocyanates
   to form urethane groups.

2. The process of claim 1 wherein component b) comprises a member selected from the group consisting of (i) unmodified organic polyisocyanates having a molecular weight of 140 to 300, (ii) lacquer polyisocyanates having a molecular weight of greater than 300 to 1,000, and (iii) urethane group-containing NCO prepolymers having a molecular weight of greater than 1,000.

3. The process of claim 1 wherein
$R^1$ represents a $C_1$–$C_4$ hydroxyalkyl radical and
$R^2$ represents a $C_1$–$C_4$ alkyl radical.

4. The process of claim 2 wherein
$R^1$ represents a $C_1$–$C_4$ hydroxyalkyl radical and
$R^2$ represents a $C_1$–$C_4$ alkyl radical.

5. The process of claim 1 wherein component a) comprises 1,3-dioxan-5-hydroxymethyl-5-methyl-2-one and/or 1,3-dioxan-5-hydroxymethyl-5-ethyl-2-one.

6. The process of claim 2 wherein component a) comprises 1,3-dioxan-5-hydroxymethyl-5-methyl-2-one and/or 1,3-dioxan-5-hydroxymethyl-5-ethyl-2-one.

7. A 1,3-dioxan-2-one group-containing oligourethane which is the urethane group-containing reaction product of
a) one or more hydroxy-functional 1,3-dioxan-2-ones corresponding to the formula

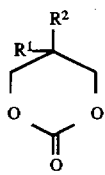

wherein
$R^1$ represents a hydroxyalkyl radical and
$R^2$ represents an alkyl radical with b) a polyisocyanate component having an average of at least two isocyanate groups per molecule and containing one or more polyisocyanates.

8. The oligourethane of claim 7 wherein component b) comprises a member selected from the group consisting of (i) unmodified organic polyisocyanates having a molecular weight of 140 to 300, (ii) lacquer polyisocyanates having a molecular weight of greater than 300 to 1,000, and (iii) urethane group-containing NCO prepolymers having a molecular weight of greater than 1,000.

9. The oligourethane of claim 7 wherein
$R^1$ represents a $C_1$–$C_4$ hydroxyalkyl radical and
$R^2$ represents a $C_1$–$C_4$ alkyl radical.

10. The oligourethane of claim 8 wherein
$R^1$ represents a $C_1$–$C_4$ hydroxyalkyl radical and
$R^2$ represents a $C_1$–$C_4$ alkyl radical.

11. The oligourethane of claim 7 wherein component a) comprises 1,3-dioxan-5-hydroxymethyl-5-methyl-2-one and/or 1,3-dioxan-5-hydroxymethyl-5-ethyl-2 -one.

12. The oligourethane of claim 8 wherein component a) comprises 1,3-dioxan-5-hydroxymethyl-5-methyl-2-one and/or 1,3-dioxan-5-hydroxymethyl-5-ethyl-2-one.

13. A coating composition having a binder which comprises the oligourethane of claim 7 optionally in combination with a compound containing at least two active hydrogen atoms.

* * * * *

UNITED STATES PATENT AND TRADEMARK OFFICE
CERTIFICATE OF CORRECTION

PATENT NO. : 5,688,891
DATED : November 18, 1997
INVENTOR(S) : Wieland Hovestadt et al It is certified that error appears in the above-indentified patent and that said Letters Patent is hereby corrected as shown below:

ON THE FACE OF THE PATENT

Correct the title by deleting "T,3-DIOXAN-2-ONE" and inserting --1,3-DIOXAN-2-ONE--.

At column 1, line 1, delete "T,3-DIOXAN-2-ONE" and insert --1,3-DIOXAN-2-ONE--.

At column 6, line 37, delete "s-caprolactan" and insert --ϵ-caprolactam--.

Signed and Sealed this

Seventeenth Day of March, 1998

Attest:

BRUCE LEHMAN

Attesting Officer        Commissioner of Patents and Trademarks